United States Patent [19]

Skatulla et al.

[11] Patent Number: 5,252,200
[45] Date of Patent: Oct. 12, 1993

[54] METHOD OF SEPARATING AN AROMATIC FROM A HYDROCARBON MIXTURE

[75] Inventors: Luzian Skatulla, Mülheim/Ruhr; Hans-Christoph Schneider, Hattingen; Hans-Jürgen Vollmer, Essen, all of Fed. Rep. of Germany

[73] Assignee: Krupp Koppers GmbH, Essen, Fed. Rep. of Germany

[21] Appl. No.: 766,445

[22] Filed: Sep. 26, 1991

[30] Foreign Application Priority Data

Dec. 15, 1990 [DE] Fed. Rep. of Germany ....... 4040145

[51] Int. Cl.$^5$ ..................... C10G 21/20; C10G 21/12
[52] U.S. Cl. .................... 208/313; 208/322; 208/326
[58] Field of Search ................ 208/313, 322, 326

[56] References Cited

U.S. PATENT DOCUMENTS

| | | | |
|---|---|---|---|
| 2,455,803 | 12/1948 | Pierotti | 208/313 |
| 3,591,490 | 7/1971 | Müller et al. | 208/313 |
| 4,519,901 | 5/1985 | Fiocco | 208/321 |
| 4,595,491 | 6/1986 | Berns | 208/326 |
| 4,664,783 | 5/1987 | Preusser et al. | 208/313 |

Primary Examiner—Theodore Morris
Assistant Examiner—Walter D. Griffin
Attorney, Agent, or Firm—Michael J. Striker

[57] ABSTRACT

The process for separating an aromatic from an entry hydrocarbon mixture also containing nonaromatics, by an extractive distillation method using an extractive distillation column with a selective solvent consisting essentially of an N-substituted Morpholine having substituents each of which contain no more than seven carbon atoms, includes distilling off the nonaromatics from the top of the extractive distillation column as a top product, drawing the aromatic and selective solvent from the extractive distillation column and subsequently separating the selective solvent from the aromatic in a separator column. The extractive distillation column is provided with an additional column portion for separation of a selective solvent residue from the separated nonaromatics without a separate top product distillation column. The hydrocarbon entry mixture is heated prior to admission to the extractive distillation column by an indirect heat exchange with selective solvent drawn from the separator column and heated to a temperature of from 130° to 150° C. to form a heated entry hydrocarbon mixture.

5 Claims, 1 Drawing Sheet

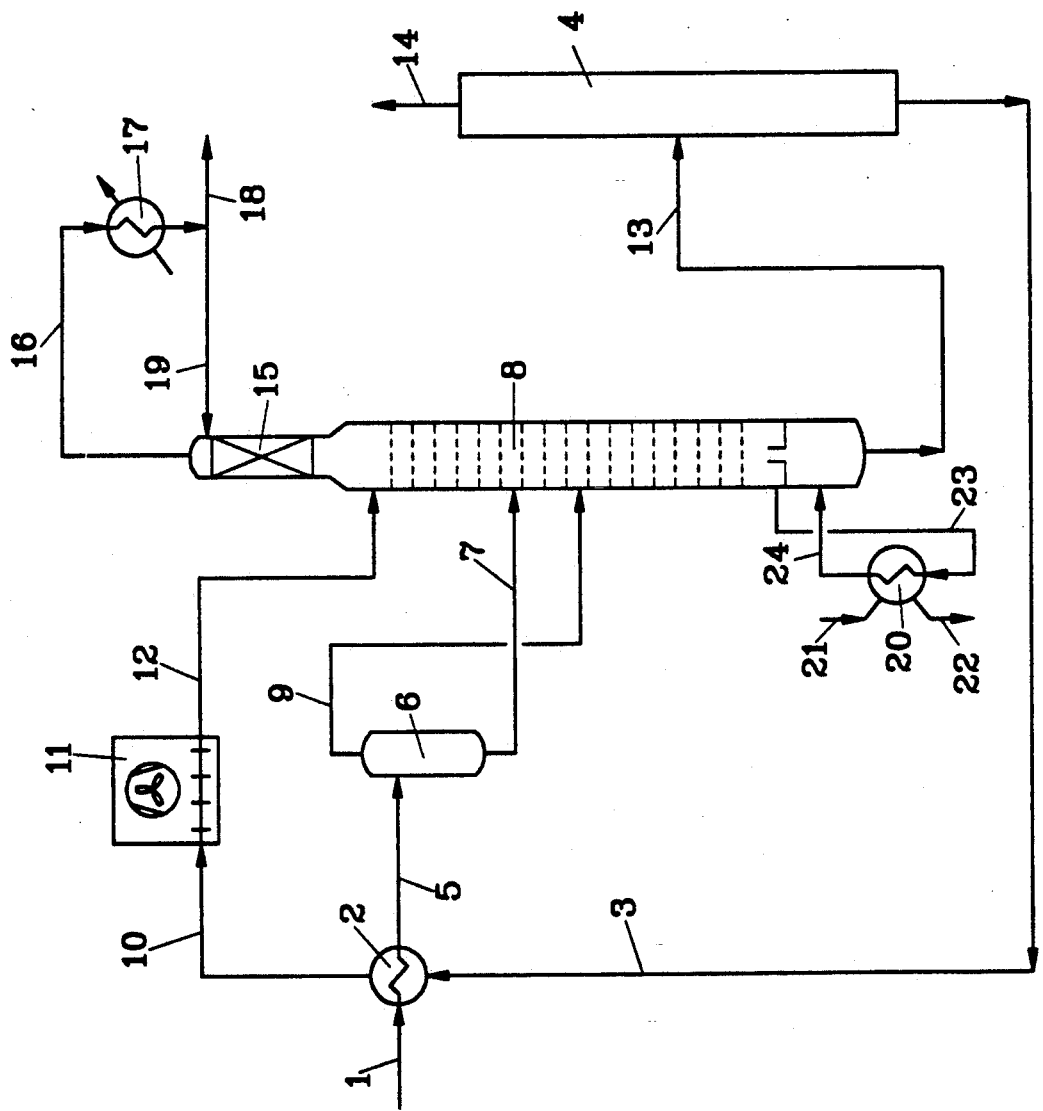

METHOD OF SEPARATING AN AROMATIC FROM A HYDROCARBON MIXTURE

BACKGROUND OF THE INVENTION

The present invention relates to a method of separating an aromatic or aromatic compound from an entry hydrocarbon mixture of arbitrary aromatic composition, especially an entry hydrocarbon mixture which can also contain nonaromatic components including paraffin, cycloparaffin, olefins, diolefins and organic sulfur compounds.

A method of separating an aromatic from an entry hydrocarbon mixture of this type is known. In this known method the separation occurs by an extractive distillation, in which N-substituted morpholine, whose substituents do not have more than seven carbon atoms, is used as selective solvent. The nonaromatic components of the entry hydrocarbon mixture are distilled off the head or top of an extractive distillation column used, while the aromatic components are drawn together with the selective solvent from the sump of the extractive distillation column and subsequently are separated from the solvent by distillation in a separator column connected to the extractive distillation column.

The above-described method of obtaining aromatic compounds has been known for many years and has proven satisfactory in the intervening time in a number of different large scale plants, particularly in the case in which N-formyl morpholine is used as a selective solvent. Normally the solvent drawn from the sump of the separator column is fed back into the extractive distillation column for reuse after suitable cooling. Up to now the solvent has been returned to the extractive distillation column at its head, because of basic process engineering considerations. Because of that the top product obtained contains a certain amount of residual solvent. This residual solvent content can amount to up to 2% by weight. Because of efficiency considerations and to obtain a top product, which is as pure as possible, it is essential that as much as possible of this solvent in the top product must be recovered.

Up to now it was standard practice that top product drawn as head product from the extractive distillation column be conducted into a separate distillation column, in which the hydrocarbons of the top product were separated from the solvent. Since the hydrocarbons of the top product must have a solvent content less than 1 ppm, this distillative separation requires a highly expensive apparatus (i.e. a separator distillation column with a high plate number) and a high energy consumption.

To decrease the high energy requirement, in German Published Patent Application 34 09 030 it has already been suggested that the distillative separation of the top product from the extractive distillation column be conducted under conditions such that the sump product obtained has a solvent content of from 20 to 75% by weight. Subsequently this sump product is separated in a separating vessel into a light phase and a heavy phase. The solvent rich heavy phase is returned to the extractive distillation column and the solvent poor light phase is fed to a raffinate distillation column. With this method of course the energy requirements for the purification of the top product are reduced. However, this still requires a separate column for the distillation of top product and also a separating vessel for the separation of heavier and lighter phase, which also means a not inconsiderable apparatus expense.

SUMMARY OF THE INVENTION

It is an object of the present invention to provide a process of the above-described type for obtaining an aromatic compound from an entry hydrocarbon mixture by extractive distillation method, in which the purification of top product obtained in the extractive distillation requires considerably less expensive apparatus, without producing additional energy consumption.

It is another object of the present invention to provide a method of the above-described type, in which the apparatus for purification of the top product obtained from the extractive distillation column is less expensive and does not consume more energy, but at the same time does not impair the purification of the top product obtained and the extracts, but instead improves their purity as much as possible.

These objects and others, which will be made more apparent hereinafter, are attained in a method for separating an aromatic from an entry hydrocarbon mixture also containing nonaromatics, wherein the nonaromatics can include at least one member from the group consisting of paraffins, cycloparaffins, olefins, diolefins and organic sulfur-containing compounds, by an extractive distillation method using an extractive distillation column with a selective solvent consisting essentially of an N-substituted morpholine having substituents each of which contain no more than seven carbon atoms, the extractive distillation method including distilling off the nonaromatics of the entry hydrocarbon mixture from the top of the extractive distillation column as a top product and drawing off the aromatic and the selective solvent together from the sump of the extractive distillation column and subsequently separating the selective solvent from the aromatic in a separator column connected to the extractive distillation column.

According to the invention, both the extractive distillation column and also the removal of residual solvent from the top product can be performed in a single common column, which has above a solvent connector or feed pipe an additional column portion for recovery of a solvent residue from the nonaromatics. Then a separate auxiliary distillation column for recovery of the solvent residue from the nonaromatics is eliminated. Another feature of the method of the invention is the heating of the entry hydrocarbon mixture prior to admission to the single common column by an indirect heat exchange to a temperature of between 130° and 150° C. with heated solvent drawn from the separator column.

According to one advantageous embodiment of the present invention the heated entry hydrocabon mixture is depressurized prior to entry into the extractive distillation column in a separator and because of that broken up or divided into a liquid and a vapor phase, which are conducted separately from each other into the extractive distillation column. The vapor phase is supplied to the extractive distillation column at a vapor phase entry point under the corresponding liquid phase entry point for the liquid phase into the extractive distillation column.

The exact position of the entry points is determined by the composition of the entry hydrocabon mixture.

The extractive distillation column suitable for performing the method according to the invention has an additional column portion above the solvent connector or fed pipe, in which the removal of the solvent residue from the top product occurs. This column portion can be provided with plates or other structures, in which the plate number is not higher than the plate number, which would be required in a separate top product distillation column.

That the problem solved by the method of the invention can be solved by it is surprising in as much as up to now one always expected that the removal of the solvent residue from the top product must occur in a separate column, so that a top product reflux can be avoided as much as possible in the extractive distillation column. The following considerations would be decisive to one considering this problem:

1. A top product reflux leads to a dilution of the solvent and thus to a reduction of the selective solvent effect, so that the desired material separation would be more difficult.

2. Highly selective solvents used—among these of course is the above-mentioned N-substituted morpholine—have only a limited solubility for the nonaromatic hydrocarbon materials to be separated. A top product reflux could lead under certain conditions to the formation of two liquid phases of different densities on the upper plates of the extractive distillation column, which could make impossible a trouble-free operation of the extractive distillation column.

Practical experience with the method of the invention has shown that the above fears did not materialize.

BRIEF DESCRIPTION OF THE DRAWING

The objects, features and advantages of the present invention will now be illustrated in more detail by the following detailed description, reference being made to the accompanying drawing in which:

The sole FIGURE is a schematic diagram showing an apparatus or plant performing the method according to the invention, in which only essential apparatus components are shown, but auxiliary devices, such as pumps, boilers, heat exchangers and measurement and regulatory devices, are not shown.

DETAILED DESCRIPTION OF THE PREFERRED EMBODIMENT

In the flow scheme shown in the drawing the entry hydrocarbon mixture is fed over the pipe 1 into the heat exchanger 2. Hot solvent at a temperature of from 130° to 150° C., which is fed over the pipe 3, is also fed to the heat exchanger 2 so that an indirect heat exchange between the entry hydrocarbon mixture and the hot solvent occurs. The heated entry hydrocarbon mixture is fed from the heat exchanger 2 into the separating vessel 6 over the pipe 5. In the separating vessel 6 it is depressurized to form a liquid phase and a vapor phase. The liquid phase is conducted over the pipe 7 into the central portion of the extractive distillation column 8. For example, the liquid phase can be introduced at the 24th plate (from the top) of an extractive distillation column of 55 plates total. Simultaneously the vapor phase is introduced over the pipe 9 under the supply location or solvent connector pipe for the liquid phase in the extractive distillation column 8. In the present case the feed of the vapor phase can occur 6 plates below the supply connection or feed pipe for the liquid phase. As has already been mentioned above, the method, if necessary, can also be performed, so that the heated entry hydrocarbon mixture coming from the heat exchanger is fed directly into the central portion of the extractive distillation column 8.

In this extractive distillation column 8, the separation of the entry hydrocarbon mixture under the influence of the solvent occurs in a known way. The solvent coming from the heat exchanger over the pipe 10 passes through the air cooler 11, in which it experiences the necessary cooling so that its temperature is between 100° and 110° C. when it is fed back into the extractive distillation column 8. The solvent flows over the plates of this column downwardly so that it receives the vaporous aromatics. The liquid sump product, which comprises the solvent and the aromatics dissolved in it, is drawn over the pipe 13 from the extractive distillation column 8 and is conducted into the separator column 4, in which this sump product, also designated as extract, is broken up into its components. The details of structure of the separator column 4 need not be described in detail here, since the work up of the extract of the extractive distillation is not the subject matter of the present invention. The aromatics are withdrawn has head products from the separator column 4 over the pipe 14, while the aromatic-free solvent collects in the sump of this column and can be conducted over the pipe 3 to the heat exchanger 2.

The nonaromatic hydrocarbons of the entry hydrocarbon mixture, which form the top product phase, climb upwardly as a vapor in the extractive distillation column. So that the residual solvent can be removed from this nonaromatic hydrocarbon, the extractive distillation column 8 has an additional column portion 15 above the solvent supply connection or feed pipe, i.e. above the entrance of the solvent connector pipe 12, into this column 8. This additional column portion 15, which can be provided with plates or other structures, forms together with the extractive distillation column 8 a combined common distillation column. In the present embodiment the column portion 15 has a somewhat smaller diameter than the standard extractive distillation column 8. In practice both portions can have the same diameter. The nonaromatic hydrocarbon liberated from the solvent residue escapes as a vapor above the top of the column portion 15 and arrives over the pipe 16 in the cooler 17, in which these hydrocarbons are condensed. The main amount of the liquid nonaromatic hydrocarbons is subsequently fed over the pipe 18 from the apparatus performing the process of the invention and further processed, while a smaller partial flow is again fed back as a reflux over the pipe 19 to the head of the column portion 15. The reflux amount is adjusted so that the obtained nonaromatics have the desired purity. Surprisingly, it has been shown that this can be attained already with a reflux of 0.5 in almost all cases in the method of the invention, while up to now a reflux ratio of 1 has been required.

For heating the circulating boiler 20 is provided at the sump of the extractive distillation column 8. This boiler 20 heats the circulating sump product by an indirect heat exchange with steam. The pipes 21 and 22 supply and remove steam and the pipes 23 and 24 supply and deliver the sump product to and from extractive distillation column 8. Understandably, additional auxiliary boilers can be arranged for additional column heating on the extractive distillation column 8. However since the column heating is not subject matter of the present invention, these features are not described in detailed herein.

The unexpectedly improved efficiency of the method of the invention is proven by the following tests described herein in the following. A pyrolyzed benzene was used as an entry hydrocarbon mixture. The throughput capacity of the plate was about 14,600 kg/h. In part a) of the experimental series (experiment 1) the purification of the top product was performed in a separate distillation column according to the conventional method. In part b) in experiment 2 for testing the method of the invention the heated hydrocarbon mixture was conducted directly into the extractive distillation column. In experiment 3 the heated entry hydrocarbon mixture was broken up into a liquid and a vapor phase and both phases separated from each other were conducted into the extractive distillation column. The experimental results are shown in the following Tables.

TABLE I

EXTRACTIVE DISTILLATION OF PRIOR ART METHOD

| Exper. No. | Inlet Temp. Entry Prod. °C. | Entry Plate Vapor/ Liquid (frm top) | Nonaromatics in Benzene ppm | Solvent in nonarom. (top product) ppm | Input Energy Gcal/h |
|---|---|---|---|---|---|
| EXP. 1 | 80 | 24 | 170 | $3 \times 10^{-3}$ | 1.806 |

TABLE II

EXTRACTIVE DISTILLATION ACCORDING TO THE INVENTION

| Exper. No. | Inlet Temp. Entry Prod. °C. | Entry Plate Vapor/ Liquid (frm top) | Nonaromatics in Benzene ppm | Solvent in nonarom. (top product) ppm | Input Energy Gcal/h |
|---|---|---|---|---|---|
| EXP. 2 | 130 | 24 | 123 | $<3 \times 10^{-3}$ | 1.803 |
| EXP. 3 | 130 | 30/20 | 98 | $<3 \times 10^{-3}$ | 1.803 |

The present experimental results show clearly that by using the method of the invention the same purity of the hydrocarbon material of the top product (nonaromatics) can be obtained despite the situation that a separate top product distillation column is not being used. Simultaneously the obtained benzene has a greatly improved purity. Because of the preheating of the entry hydrocarbon mixture, the energy requirements of the method of the invention have been slightly reduced in comparison to those of the prior art. Because of the omission of the separate top product distillation column from the invention a clear saving in apparatus and maintenance cost however has been obtained.

While the invention has been illustrated and as embodied in a method of separating an aromatic compound from a hydrocarbon mixture of arbitrary aromatic content, it is not intended to be limited to the details shown described, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. In a process for separating an aromatic from an entry hydrocarbon mixture also containing nonaromatics, wherein said nonaromatics can include at least one member from the group consisting of paraffins, cycloparaffins, olefins, diolefins and organic sulfur-containing compounds, by an extractive distillation method using an extractive distillation column with a selective solvent, said selective solvent consisting essentially of an N-substituted Morpholine having substituents each of which contain no more than seven carbon atoms, said extractive distillation column having a top, a sump and a solvent connector pipe through which the selective solvent is fed, said extractive distillation method including distilling off the nonaromatics of the entry hydrocarbon mixture from the top of the extractive distillation column as a top product and drawing off the aromatic and the selective solvent together from the sump of the extractive distillation column and subsequently separating the selective solvent from the aromatic in a separator column connected to the extractive distillation column, the improvement comprising providing the extractive distillation column with an additional column portion for separation of a selective solvent residue from the top product containing the nonaromatics, performing an extractive distillation with the selective solvent and the separation of the selective solvent residue from the nonaromatics in a single common distillation column comprising the extractive distillation column and the additional column portion above the solvent connector pipe of the extractive distillation column, and heating the hydrocarbon entry mixture prior to admission to the extractive distillation column by an indirect heat exchange with the selective solvent drawn from the separator column and heated to a temperature of from 130° to 150° C. to form a heated entry hydrocarbon mixture.

2. The improvement as defined in claim 1, further comprising breaking up the heated entry hydrocarbon mixture into a liquid phase and a vapor phase prior to introduction into the extractive distillation column and conducting the liquid phase and the vapor phase into the extractive distillation column separately at a liquid phase entry point and a vapor phase entry point, the vapor phase entry point being below the liquid phase entry point.

3. The improvement as defined in claim 1, further comprising providing a reflux in the additional column portion and wherein a reflux amount in the additional column portion is adjusted to provide a reflux ratio of about 0.5.

4. A process for separating an aromatic from an entry hydrocarbon mixture also containing nonaromatics, wherein said nonaromatics can include at least one member from the group consisting of paraffins, cycloparaffins, olefins, diolefins and organic sulfur-containing compounds, by an extractive distillation method with a selective solvent using a single common distillation column comprising an extractive distillation column and an additional column portion for recovery of a selective solvent residue from the nonaromatics, said selective solvent consisting essentially of an N-substituted Morpholine having substituents each of which contain no more than seven carbon atoms, said single common distillation column having a sump and a solvent connector pipe through which the selective solvent is fed, said process comprising the steps of distilling off the nonaromatics of the entry hydrocarbon mixture from the single common distillation column, drawing off the aromatic and the selective solvent together from the sump of the single common distillation column, subsequently separating the selective solvent from the aromatic in a separator column connected to the single common distillation column, drawing off the selective solvent from a sump of the separator column and heating the selective solvent so separated to a temperature of from 130° to 150° C., heating the entry hydrocarbon mixture with the selective solvent drawn from the sump of the separator column heated to from 130° to 150° C. to form a heated entry hydrocarbon mixture, and recovering the selective solvent residue from the nonaromatics in the additional column portion of the single common distillation column without using another separate distillation column.

5. The process according to claim 4, further comprising the steps of breaking up the heated entry hydrocarbon mixture into a liquid phase and a vapor phase prior to introduction into the extractive distillation column, conducting the liquid phase and the vapor phase into the extractive distillation column separately at a liquid phase entry point and a vapor phase entry point, the vapor phase entry point being below the liquid phase entry point and setting a reflux ratio in the additional column portion to about 0.5.

* * * * *